US009522401B2

(12) United States Patent
Hayden et al.

(10) Patent No.: US 9,522,401 B2
(45) Date of Patent: Dec. 20, 2016

(54) DEVICE AND METHOD FOR CONCENTRATING AND DETECTING MAGNETICALLY MARKED CELLS IN LAMINARLY FLOWING MEDIA

(75) Inventors: Oliver Hayden, Herzogenaurach (DE); Manfred Rührig, Lauf a.d. Pegnitz (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 258 days.

(21) Appl. No.: 13/254,731

(22) PCT Filed: Mar. 3, 2010

(86) PCT No.: PCT/EP2010/052697
§ 371 (c)(1),
(2), (4) Date: Sep. 2, 2011

(87) PCT Pub. No.: WO2010/100192
PCT Pub. Date: Sep. 10, 2010

(65) Prior Publication Data
US 2011/0315635 A1 Dec. 29, 2011

(30) Foreign Application Priority Data
Mar. 6, 2009 (DE) .................. 10 2009 012 108

(51) Int. Cl.
*B03C 1/28* (2006.01)
*G01N 1/40* (2006.01)
(Continued)

(52) U.S. Cl.
CPC .......... *B03C 1/288* (2013.01); *B01L 3/502761* (2013.01); *B03C 1/0335* (2013.01);
(Continued)

(58) Field of Classification Search
CPC .... B03C 1/288; B03C 1/0335; B03C 2201/26; G01N 1/40; B01L 3/502761; B01L 2400/043; B01L 2300/0877
See application file for complete search history.

(56) References Cited

U.S. PATENT DOCUMENTS 5,475,304 A * 12/1995 Prinz ................. G01B 7/02
324/207.21
5,932,097 A * 8/1999 Wilson ................. 210/222
(Continued)

FOREIGN PATENT DOCUMENTS

DE 19706617 C1 4/1998
EP 1916032 A1 4/2008
(Continued)

OTHER PUBLICATIONS

N. Pamme and A. Manz, "On-Chip Free-Flow Magnetophoresis: Continuous Flow Separation of Magnetic Particles and Agglomerates", Anal. Chem., 2004, 76, 7250-7256; Others.
(Continued)

*Primary Examiner* — David C Mellon
(74) *Attorney, Agent, or Firm* — Slayden Grubert Beard PLLC

(57) ABSTRACT

The embodiments relate to a device and to a method for concentrating and detecting cells in flowing media, in particular magnetically marked cells in complex media such as blood. For this purpose, at least one magnet is used, said magnet being coupled to at least one magnetoresistance. In the method the cells are concentrated on a magnetoresistor by the least one external magnetic field having a pulsed operation.

4 Claims, 2 Drawing Sheets

(51) Int. Cl.
  *B01L 3/00* (2006.01)
  *B03C 1/033* (2006.01)
(52) U.S. Cl.
  CPC ........ *G01N 1/40* (2013.01); *B01L 2300/0877* (2013.01); *B01L 2400/043* (2013.01); *B03C 2201/26* (2013.01)

(56) References Cited

U.S. PATENT DOCUMENTS

| | | | |
|---|---|---|---|
| 6,736,978 | B1 | 5/2004 | Dawson |
| 7,300,631 | B2 * | 11/2007 | Miller ............... B01L 3/502761 422/68.1 |
| 2004/0219695 | A1 | 11/2004 | Fox |
| 2007/0020770 | A1 | 1/2007 | Chalmers |
| 2007/0114180 | A1 * | 5/2007 | Ramanathan et al. ........ 210/695 |
| 2008/0024118 | A1 | 1/2008 | Kahlman |
| 2008/0191688 | A1 | 8/2008 | Kahlman |
| 2010/0273184 | A1 * | 10/2010 | Bar ................... G01N 15/1031 435/7.2 |
| 2013/0004982 | A1 * | 1/2013 | Bar ................... G01N 15/1031 435/29 |

FOREIGN PATENT DOCUMENTS

| | | |
|---|---|---|
| WO | WO 2008001261 | 1/2008 |
| WO | WO 2008007291 | 1/2008 |
| WO | WO 2008102218 | 8/2008 |

OTHER PUBLICATIONS

J. Schotter, P. B. Kamp, A. Becker, A. Puhler, G. Reiss and H. Brückl, "Comparison of a prototype magnetoresistive biosensor to standard fluorescent DNA detection", Biosensors & Bioelectronics, 2004, 19, 1149-1156; Others.

Pekas, N., Granger, M., Tondra, M., Popple, A. and Porter, M. D, "Magnetic particle diverter in an integrated microfluidic format" Journal of Magnetism and Magnetic Materials, 293, pp. 584-588, (2005); Others.

M. Tondra, M. Granger, R. Fuerst, M. Porter, C. Nordman, J. Taylor, and S. Akou, "Design of Integrated Microfluidic Device for Sorting Magnetic Beads in Biological Assays" IEEE Transactions on Magnetics 37, (2001), pp. 2621-2623; Others.

N. Pekas, M. D. Porter, M. Tondra, A. Popple and A. Jander, "Giant magnetoresistance monitoring of magnetic picodroplets in an integrated microfluidic system" Appl. Phys. Lett., 2004, 85, 4783; Others.

D. W. Inglis, R. Riehn, R. H. Austin and J. C. Sturm, "Continuous microfluidic immunomagnetic cell separation" Appl. Phys. Lett., 2004, 85, 5093; Others.

Tamanaha C. R. et al.; "Magnetic labeling, deteting, and system integration"; Biosensors and Bioelectrnics, Elsevier, Bd. 24, (2008), Nr. 1, pp. 1-13.

Edelstein R.L. et al.; "The BARC biosensor applied to the detection of biological warfare agents", Biosensors & Bioelectronics, Bd., 14, Nr. 10/11, 2000, pp. 805-813.

* cited by examiner (A)

(B)

DEVICE AND METHOD FOR CONCENTRATING AND DETECTING MAGNETICALLY MARKED CELLS IN LAMINARLY FLOWING MEDIA

CROSS REFERENCE TO RELATED APPLICATIONS

This application is the U.S. national stage of International Application No. PCT/EP2010/052697, filed Mar. 3, 2010 and claims the benefit thereof. The International Application claims the benefits of German Application No. 10 2009 012 108.0, filed on Mar. 6, 2009, both applications are incorporated by reference herein in their entirety.

BACKGROUND

The embodiments relate to a device and a method for concentrating and detecting cells in flowing media, in particular, marked cells in complex media such as for example blood.

Until now, there has been no non-optical solution for carrying out reliable individual cell detection with a magnetic flow cytometer in laminar flow.

The currently known technical solutions for individual cell detection are predominantly optical methods for detecting cells with fluorescent markers or by scattered light from a suspension in flow channels. Magnetic methods are mainly restricted to concentrating magnetically marked cells, and to biosensors comprising magnetoresistive transducers.

The following magnetic methods are known:
1) Applying an external magnetic field perpendicularly to the flow direction. In a gradient field, it is also possible to a limited extent to sort analytes according to size and magnetic moment, cf. N. Pamme and A. Manz, Anal. Chem., 2004, 76, 7250.
2) Installing a ferromagnetic conductor at the bottom of the separating chamber. Owing to the local field gradient, magnetizable cells are concentrated at the bottom along the ferromagnetic conductor and separated at flow rates of <1 mm/s of unmarked cells, in this respect, see D. W. Inglis, R. Riehn, R. H. Austin and J. C. Sturm, Appl. Phys. Lett., 2004, 85, 5093.
3) A current conductor is fitted at the bottom of the separating chamber. The flow current flow induces a magnetic field which in turn—as mentioned in point 2—can be used to concentrate cells (flow rate: 6 nl/min in microfluidic channels) Pekas, N., Granger, M., Tondra, M., Popple, A. and Porter, M. D, Journal of Magnetism and Magnetic Materials, 293, pp. 584-588, (2005). c) M. Tondra, M. Granger, R. Fuerst, M. Porter, C. Nordman, J. Taylor, and S. Akou, IEEE Transactions on Magnetics 37, (2001), pp. 2621-2623.

The detection of marked cells with embedded GMR sensors can to date be carried out only statically in analogy with an assay, and not dynamically i.e. for example in laminar flow. Cf: J. Schotter, P. B. Kamp, A. Becker, A. Puhler, G. Reiss and H. Brückl, Biosens. Bioelectron., 2004, 19, 1149.

Commercial manufacturers of sensors having magnetoresistive elements only offer assays for DNA and protein analysis for in vitro diagnosis. In this regard, reference may for example be made to the Internet addresses of magnabiosciences.com, diagnsticbiosensors.com, seahawkbio.com and san.rr.com/magnesensors.

In known magnetic flow cytometers, cells which are marked with magnetic markers, for example superparamagnetic labels, are transported in a flow chamber near the surface over a magnetoresistive sensor (for example a GMR (giant magnetoresistance sensor), as described for example by N. Pekas, M. D. Porter, M. Tondra, A. Popple and A. Jander, Appl. Phys. Lett., 2004, 85, 4783.

A problem with this is that the required proximity of the marked cell to the sensor is not achieved, as the leakage magnetic scattered field due to the magnetic markers decays with the third power of the distance from the sensor. With the previously known methods, it is therefore generally far from possible to detect all the marked cells.

SUMMARY

It is therefore an aspect of the embodiments to overcome the disadvantages of the prior art and to provide a device and a method for individual cell detection in a flowing medium.

This aspect is achieved by the subject matter as disclosed in the claims, the description and the figures.

Accordingly, the embodiments provide a device for concentrating and detecting cells, where at least one magnetoresistor is arranged in an external magnetic field surrounding it below a channel, in which a laminar flow of a medium having magnetically marked cells flows. The embodiments also provide a method for concentrating and detecting magnetically marked cells in a laminarly flowing medium, wherein cells are concentrated on a magnetoresistor by an external magnetic field.

The embodiments thus for the first time disclose the technique by which concentration of marked cells can be achieved directly on the magnetoresistors by using an external magnetic field, so that almost 100% detection of the marked cells is achievable.

These are precisely cells such as occur in living beings, for example animals/humans.

By the flow cytometry presented here, it is almost possible for individual marked cells to be counted dynamically in the flowing medium with an acquisition rate of close to 100% when flowing over the GMR component.

In particular for diseases which are hard to detect, such as cancer, it is sometimes necessary for from 1 to 100 cells to be quantifiable in about 10 ml of whole blood.

According to an advantageous embodiment,
a. Individual marked cells in a complex matrix such as blood or partially purified (typically 1:1000 to 1:1,000,000) are conveyed past the substrate surface (as close as possible to the GMR sensor) while they are contained in the flowing medium
b. On the surface, they are aligned with respect to the GMR sensor in the laminar flow (cells must not flow stochastically distributed over the substrate with the sensor/sensors)
c. Cells are detected individually ("counted"; thus magnetic flow cytometry); to this end, a substantially high signal-to-noise ratio is advantageous.

According to an advantageous embodiment of the method, the magnetic field is applied in such a way that amplification of the gradient of the magnetic field takes place directly below the GMR sensors, so that the point of entry of the magnetic field lines into the sample space lies as close as possible to the GMR sensors.

To this end, according to an advantageous embodiment of the device, the magnet is arranged directly below the GMR sensors.

The embodiment in which the magnet for the external magnetic field surrounding the magnetoresistors is chamfered on one or both sides, so that flux concentration and an increase in the magnetic field gradient results therefrom, is advantageous in particular.

The cell detection with magnetoresistors is carried out most simply with technically advanced sensors such as anisotropic magnetoresistance (AMR), GMR and/or tunneling magnetoresistance (TMR) sensors, the latter two advantageously being configured as so-called spin valves.

The effect of the laminar flow is that the cells are transported in the liquid flow without turbulence. However, cells which come in contact with the surface are caused to rotate owing to shear forces which occur and the flow profile. According to the embodiments, the effect is utilized on the one hand to guide as many of the marked cells as possible to the magnetoresistors, and on the other hand to bring the statistically distributed immunomagnetic markers on the cell surface close to the GMR sensors by "rolling".

The concentration of cells in a magnetic field gradient, which in the present case is used only for the cell separation, is suitable for concentrating the marked cells from the laminar flow onto the substrate surface with the magnetoresistors in a controlled way as a function of the flow rate and number of magnetic labels per cell. Furthermore the magnetic force, and therefore the shear force or holding force on the concentrated cells, can be varied via the flow speed and the strength of the gradient without preventing transport of unmarked cells along the microfluidic channel.

Preferably, this measurement object is achieved by a combination of the following components of a measurement system:
   d. A GMR sensor has a dimension which corresponds to the diameter of an individual cell (typically 5-40 µm), in order to achieve a high signal-to-noise ratio and detect a signal from just one cell
   e. In order to be able to measure individual cells in a large sample volume, they are conveyed in a flowing medium
   f. An external magnetic gradient field is preferably used in order to convey stochastically distributed and marked cells in a microfluidic channel onto the substrate surface (typically, the distance from the cell to the GMR sensor is 0-1 µm); the signal-to-noise ratio can then be increased
   g. The flowing medium is advantageously laminar, since turbulence can lead to a reduction in the acquisition rate of marked cells. Typical channels have a cross section with a width of 100-1000 µm and a height of 100-1000 µm. This means that a GMR sensor with cell dimensions is substantially smaller than the channel size.

The individual marked cells are conveyed in a controlled way into the immediate vicinity of the substrate in the flowing medium. Stochastic distribution of marked cells on the substrate surface leads to counting losses (for example, ~90% loss with a 10 µm GMR in a 100 µm channel). Cells are therefore conveyed along e.g. ferromagnetic strips directly onto a sensor. This measurement arrangement also has the advantage that, in the ideal case, only one single GMR sensor is necessary in order to count all the marked cells.

BRIEF DESCRIPTION OF THE DRAWINGS

These and other aspects and advantages will become more apparent and more readily appreciated from the following description of the exemplary embodiments, taken in conjunction with the accompanying drawings of which.

DETAILED DESCRIPTION OF THE PREFERRED EMBODIMENT

Figure 1:
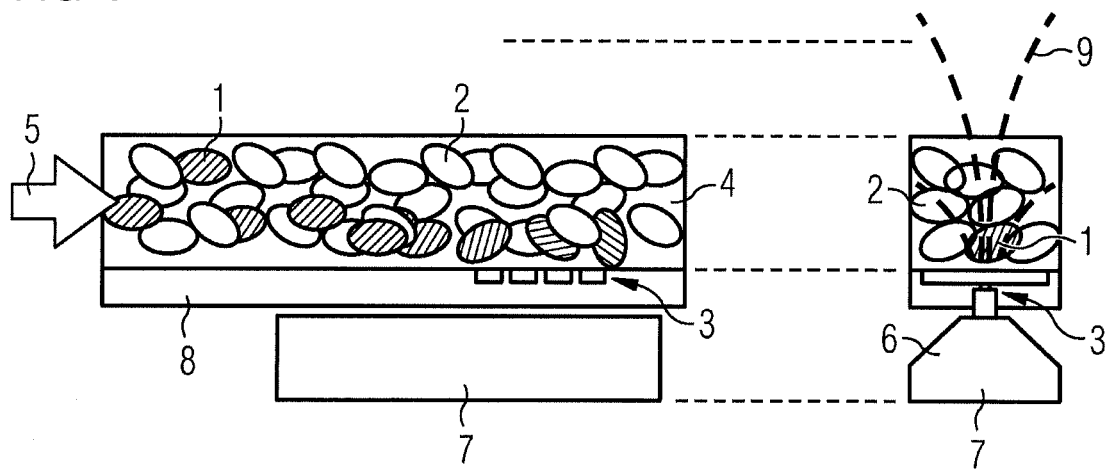
FIG. 1 shows channel cell concentration.

Reference will now be made in detail to the preferred embodiments, examples of which are illustrated in the accompanying drawings, wherein like reference numerals refer to like elements throughout.

FIG. 1 shows two cross sections through an embodiment of a microfluidic channel according to the embodiments: on the left a cross section along the flow direction and on the right a cross section perpendicular to the flow direction.

FIG. 1 schematically shows the process of cell concentration on the substrate surface 8 with the GMR sensors.

A lengthwise side cross section of a microfluidic channel 4 in which a laminar flow flows, as indicated by the arrow 5, can be seen on the left-hand part of the figure.

In the vicinity of the arrow 5, there are marked cells 1 and unmarked cells 2, which move uniformly distributed in the laminar flow. A magnet 7 is arranged somewhat to the right thereof and below the microfluidic channel 4; the concentration of the marked cells on the bottom/substrate 8 of the channel inside the magnetic field gradient 7 can be seen immediately. The GMR sensors, like all magnetoresistors, may in this case also be arranged on the side walls of the channel wall and/or at the top of the channel. In turn somewhat further to the right, i.e. in the flow direction, there are a plurality of GMR sensors 3 on the bottom/substrate 8 of the channel. Owing to the "cell rolling" on the channel bottom and the concentration of the marked cells by the external magnetic field, it is also possible for as many of the marked cells as possible to be actually detected by the GMR sensors.

Here, the concentration of cells with superparamagnetic markers 1 from a complex medium in a magnetic field 9 is shown. The laminar flow 5 prevents turbulence of the cells 1 and 2. By adjustment of the magnetic field strength, the cells 1, 2 can roll along the substrate surface 8 and thus come in closest contact with the GMR sensors 3. The strength of the magnetic field should not however hinder the transport of the marked cells in the microfluidic channel; this may be achieved for example by suitable pulsed operation as well as by the symmetry of the gradient field.

On the right and at a distance from the left-hand part of FIG. 1, the microfluidic channel 4 can be seen in cross section through the flow direction. The field lines 9 of the magnetic field are visible, having their origin at the GMR sensors 3 and therefore causing gradient amplification of the magnetic field. This is crucially attributable to the fact that the magnet 7 has at least one chamfer 6 in the direction of the GMR sensors, and preferably 2 chamfers 6 as shown.

Figure 2:
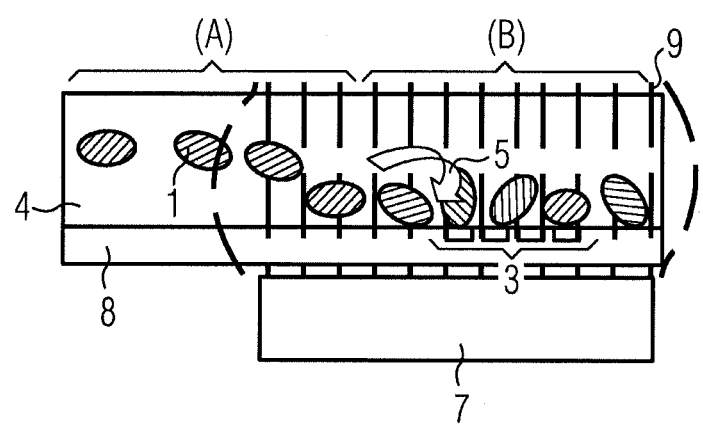
FIG. 2 shows a cross section of FIG. 2.

FIG. 2 shows the same image as FIG. 1 in longitudinal cross section, and illustrates the cell rolling inside the laminar flow 5. The three phases of the cell rolling can be seen: first (A) the concentration of the marked cells 1 on the substrate surface of the bottom 8 of the microfluidic channel 4 in the magnetic field 9 then (B) the cell rolling over the sensor surface while (C) the cell detection takes place.

According to an advantageous embodiment, in order to carry out cell detection with the GMR sensor (for example, as a Wheatstone bridge circuit), for example for continuous concentration of the cells, the gradient magnetic field (~100 mT with dB/dx equal to a few 10-100 T/m; depending on the loading of the cells with superparamagnetic particles) is pulsed. The detection of the marked cells is carried out in a weak measurement magnetic field of ~1 mT.

Figure 3:
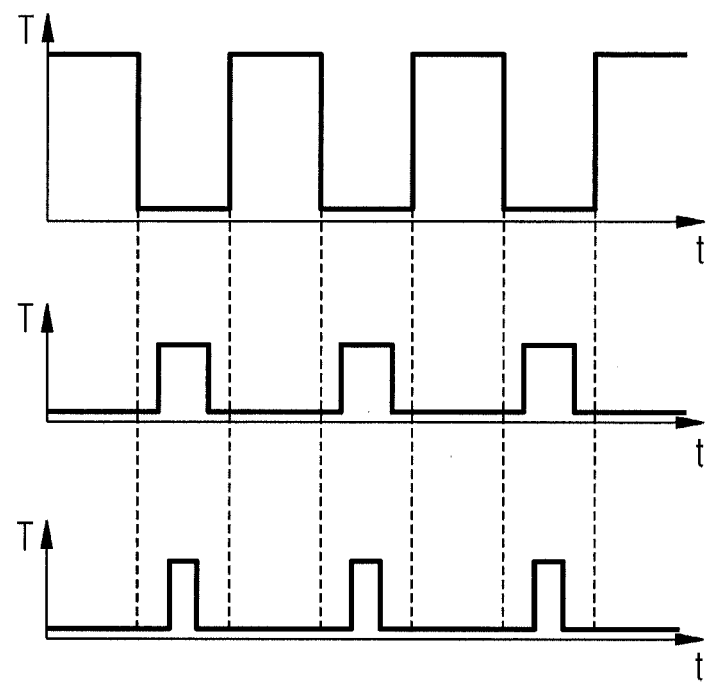
FIG. 3 shows magnetic field strength over time.

FIG. 3 shows in chronological sequence the strength of the magnetic field for the cell concentration, cell detection and the GMR measurement. The time is plotted on the X axis, so that it can be seen that two magnetic field strengths are always applied in chronological alternation. A method for continuous cell concentration and cell detection can thus be carried out by a sequence of pulsed magnetic fields.

The cyclic sequence of (1) concentration, (2)+(3) measurement for a continuous measurement, which is graphically represented in pictorial fashion, can be seen in FIG. 3. The measurement and concentration of the cells can therefore be preformed or controlled independently of one another in the kHz range. FIG. 3 shows the way in which, at the very top, cell concentration inside the microfluidic channel takes place with a "strong magnetic field and long pulse times". Below this, there is a graph which shows that a weaker magnetic field with a shorter pulse time is used for the cell detection. Lastly, the bottom graph shows how the GMR measurement is accomplished with a weak magnetic field and a short pulse time.

Figure 4:
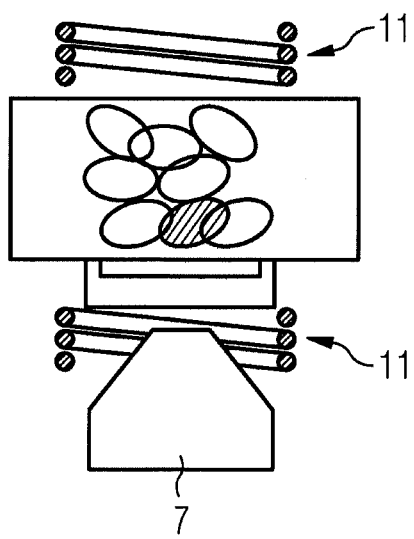
FIG. 4 shows another channel cross section.
Figure 4:
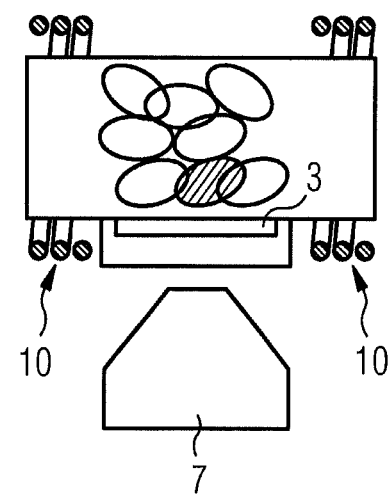

FIG. 4 in turn shows a microfluidic channel, again in a cross section perpendicular to the flow direction, as on the right-hand side in FIG. 1.

For the GMR measurement, the measurement magnetic field may be applied perpendicularly to or in the same plane as the GMR sensors (FIG. 4). In this case, the magnet (magnet yoke) of the gradient magnetic field may be used to adjust a gradient in the measurement magnetic field, in order to achieve local detuning of the bridge arms of the GMR measurement bridge. This detuning represents the measurement signal for the concentration of the magnetic particles in the sensor region. In one possible form of configuration, the measurement magnetic field may additionally be modulated as a function of time as well, for example, in order to be able to measure by means of a lock-in technique and suppress the low-frequency noise components (1/f noise), so as to improve the signal-to-noise ratio.

According to an advantageous embodiment, concentration and detection are carried out with pulsed magnetic fields as shown in FIG. 3. FIG. 4 shows the schematic arrangement of the magnets or coils 7, 10 and 11 for concentration and detection around the microfluidic channel 4. For example, the magnet 7 for the strong magnetic field for the concentration is applied below the GMR sensors and the coils 10 and 11 for the weak magnetic field for the detection are applied perpendicularly to the GMR sensor. The two fields can be controlled separately with 2 magnets, the weak magnetic field preferably being applied in the plane of the sensor.

The essential advantages of the device according to the embodiments and the method according to the embodiments are as follows:
1) Continuous measurement method in order to concentrate magnetically marked cells and detect them in continuous flow.
2) The concentration of the cells, or the shear force exerted on the cells, can be controlled by the magnetic field strength and the flow speed.
3) Marked cells are close to the surface and can be detected sensitively with magnetoresistive components.
4) The proposed method allows use over a large area for multiplexing (for example an array of GMR sensors).
5) The "cell rolling" can be adapted to the application with the aid of surface-functionalized microfluidic channels. The functionalization may for example be carried out with receptors (selectins), biological components (proteins, polysaccharides), by SAMs (self-assembled monolayers) or by silanization.
6) Concentration of marked cells, such as infrequent cancer cells (CTCs; circulating tumor cells), tumor stem cells, inflammation cells, stem cells, bacteria or yeasts, can precede the actual detection in the flowing medium.
7) The magnetic detection can be combined with optical methods (FACS, fluorescence, absorption) and electrical methods (impedance, dielectrophoresis).
8) Applications in the human field are, inter alia: oncology, regenerative medicine, infectology, clinical diagnosis, clinical chemistry, imaging.

A description has been provided with particular reference to preferred embodiments thereof and examples, but it will be understood that variations and modifications can be effected within the spirit and scope of the claims which may include the phrase "at least one of A, B and C" as an alternative expression that means one or more of A, B and C may be used, contrary to the holding in *Superguide* v. *DIRECTV*, 358 F3d 870, 69 USPQ2d 1865 (Fed. Cir. 2004).

The invention claimed is:

1. A method, comprising:
concentrating and detecting magnetically marked cells in a laminarly flowing medium,
wherein the magnetically marked cells are concentrated on a magnetoresistor by a gradient of at least a first external magnetic field having a first amplitude,
wherein the magnetically marked cells are detected in a gradient of at least a second external magnetic field having a second amplitude, wherein the first amplitude is larger than the second amplitude, wherein the first external magnetic field is perpendicular to the second external magnetic field, and wherein the first external magnetic field is switched off in each measuring time interval during which the second external magnetic field is switched on.

2. The method as claimed in claim 1,
wherein the first external magnetic field concentrates the magnetically marked cells on the magnetoresistor in a channel; and
wherein the first and second external magnetic fields are both pulsed in operation.

3. The method as claimed in claim 2, wherein the first and second external magnetic fields, which are applied in pulsed fashion, differ in strength by orders of magnitude.

4. The method as claimed in claim 3, wherein the first external magnetic field and the second external magnetic field differ in strength by at least a factor of 100.

* * * * *